(12) United States Patent
Halden

(10) Patent No.: US 8,691,582 B2
(45) Date of Patent: Apr. 8, 2014

(54) METHODS AND SYSTEMS FOR FLUID EXAMINATION AND REMEDIATION

(71) Applicant: Rolf U. Halden, Phoenix, AZ (US)

(72) Inventor: Rolf U. Halden, Phoenix, AZ (US)

(73) Assignee: Arizona Board of Regents, Scottsdale, AZ (US)

( * ) Notice: Subject to any disclaimer, the term of this patent is extended or adjusted under 35 U.S.C. 154(b) by 0 days.

(21) Appl. No.: 13/681,125

(22) Filed: Nov. 19, 2012

(65) Prior Publication Data

US 2013/0095517 A1 Apr. 18, 2013

Related U.S. Application Data

(62) Division of application No. 12/702,033, filed on Feb. 8, 2010, now Pat. No. 8,338,182.

(51) Int. Cl.
*G01N 33/24* (2006.01)
*G01N 33/00* (2006.01)

(52) U.S. Cl.
USPC .............................................. 436/28; 436/25

(58) Field of Classification Search
USPC ......... 436/28, 25; 204/403.1, 403.06, 403.01, 204/400, 194
See application file for complete search history.

(56) References Cited

U.S. PATENT DOCUMENTS

| | | | |
|---|---|---|---|
| 2,609,878 A | 9/1952 | Halliburton | |
| 5,138,890 A | 8/1992 | Wood | |
| 5,349,874 A | 9/1994 | Schapira | |
| 5,369,011 A | 11/1994 | Ebersole | |
| 5,559,295 A | 9/1996 | Sheryll | |
| 5,686,299 A | 11/1997 | Colwell | |
| 6,004,766 A | 12/1999 | Atrache | |
| 6,174,673 B1 | 1/2001 | Short | |
| 6,365,368 B1 | 4/2002 | Minnich | |
| 6,561,046 B1 | 5/2003 | Taylor | |
| 6,649,403 B1* | 11/2003 | McDevitt et al. | 435/288.5 |
| 7,662,618 B2 | 2/2010 | Halden | |
| 2004/0180334 A1* | 9/2004 | Halden | 435/5 |
| 2005/0074834 A1 | 4/2005 | Chaplen | |
| 2007/0161076 A1* | 7/2007 | Halden | 435/34 |

FOREIGN PATENT DOCUMENTS

| | | |
|---|---|---|
| WO | WO 2004/081530 | 9/2004 |
| WO | WO 2005/076887 | 8/2005 |
| WO | WO 2009/105241 | 8/2009 |

OTHER PUBLICATIONS

Halden, R et al, "Removal of dibenzofuran, dibenzo-p-dioxin, and 2-chlorodibenzo-p-dioxin from soils inoculated with *Sphingomonas* sp. strain RW1." Appl. Environ. Microbiol., 65:2246-2249 (1999) USA.

(Continued)

*Primary Examiner* — Christine T Mui
(74) *Attorney, Agent, or Firm* — George A. Leone; Citadel Patent Law

(57) ABSTRACT

A method for in situ monitoring within a specified environment. The method includes locating a housing in a well, wherein a set of pumps and a plurality of test beds are inserted. Each of the set of pumps are controlled by signals from the control system to push water from each pump into one of the plurality of separate test beds where, after flowing through each of the test beds, effluent flows into an effluent storage device.

26 Claims, 17 Drawing Sheets

(56) References Cited

OTHER PUBLICATIONS

Halden, R et al, "Transformation of mono- and dichlorinated phenoxybenzoates by phenoxybenzoate-dioxygenase in *Pseudomonas pseudoalcaligenes* POB310 and a modified diarylether-metabolizing bacterium," Biotechnol. Bioeng. 69:107-112 (2000) USA.
Halden, R et al, "Degradation of 3-phenoxybenzoic acid in soil by *Pseudomonas pseudoalcaligenes* POB310 (pPOB)," Appl. Environ. Microbiol. 65:3354-3359 (1999) USA.
Lowe, M. et al, "Geochemistry and microbial diversity of a trichloroethene-contaminated Superfund site undergoing intrinsic in situ reductive dechlorination," FEMS Microbiology Ecology 40:123-134 (2002) USA.
Vancheeswaran, S et al, "Abiotic and biological transformation of tetraalkoxysilanes and trichloroethene/cis-1,2-dichloroethene cometabolism driven by tetrabutoxysilane-degrading microorganisms," Environ. Sci. Technol. 33:1077-1085 (1999) USA.
Vancheeswaran, S et al, "Intrinsic remediation of trichloroethene driven by tetraalkoxysilanes as co-contaminants: results from microcosm and field studies," Remediation 13/14:7-25 (2003) USA.
Halden, R. U. Parallel In Situ Screening of Remediation Strategies for Improved Decision Making, Remedial Design, and Cost Savings. Environmental Security Technology Certification Program (ESTCP). http://www.estcp.org/Technology/ER-0914-FS.cfm USA.
Chalew, T. et al. (2009) Environmental Exposure of Aquatic and Terrestrial Biota to Triclosan and Triclocarban. J Am Water Resour Assoc 45(1):3-13 USA.
Colqhoun, D. R., et al. (2009) Global Screening of Human Cord Blood Proteomes for Biomarkers of Toxic Exposure. Environ Health Persp 117(5):832-838 USA.
Deo, R. P. et al (2010) Effect of Filtration on the Quality of Monitoring Data Reported for Organic Compounds during Wastewater Treatment. J. Environ. Monit. Feb. 2010 12(2):478-83 USA.
Deo, R. P. et al (2009) Empirical Model for Predicting Concentrations of Refractory Hydrophobic Organic Compounds in Digested Sludge. Environ Chem. Dec. 18, 2009;6(6):544 USA.
Heidler, J. et al (2009) Fate of Organohalogens in U.S. Wastewater Treatment Plants and Estimated Chemical Releases to Soils Nationwide from Biosolids Recycling. J. Environ. Monit., 2009, 11, 2207-2215 USA.
Heider, J. et al (2008) Critical Review. Meta-analysis of Mass Balances for Monitoring Chemical Fate during Wastewater Treatment. Environ. Sci. Technol. 42:6324-6332 USA.
Higgins, C. P. et al (2009) Bioaccumulation of Triclocarban in *Lumbriculus variegates*. Environ. Toxicol. Chem. 65:141-148 USA.
Miller, T. R. et al (2007) Bacterial Community Analysis of Shallow Groundwater Undergoing Sequential Anaerobic and Aerobic Chloroethene Biotransformation. FEMS Microbiol. Ecol. 60(2):299-311 USA.
Miller, T. R. et al (2008) Fate of Triclosan and Triclocarban in Estuarine Sediment. Environ. Sci. Technol. 42:4570-4576 USA.
Rittmann, B. E. et al (2008) Pre-genomic, Genomic and Postgenomic Study of Microbial Communities Involved in Bioenergy. Nature Micro Rev 6(8):604-612 UK.
Young, T.A. t al (2008) Ab Initio and In Situ Comparison of Organic Wastewater Compounds as Indicators of Sewage-derived Microbes in Surface Waters. Environ. Sci. Technol. 42(9):3335-3340 USA.
Zhang, Y., N. et al (2009) Protein Modifications Relate to Phage Resistance in a Marine Roseobacter. Aquatic Microbial Ecology. 55(2):203-207 USA.
Zhao, Y., K. et al (2009) Searching for a "Hidden" Prophage in a Marine Bacterium. Appl. Environ. Microbiol. Jan. 2010 76(2):589-595 USA.
U.S. Appl. No. 12/702,033, Restriction Requirement, Feb. 22, 2012.
U.S. Appl. No. 12/702,033, Response to Restriction Requirement, Mar. 14, 2012.
U.S. Appl. No. 12/702,033, Non-Final Office Action, Apr. 12, 2012.
U.S. Appl. No. 12/702,033, Response to Non-Final Office Action, Aug. 10, 2012.
U.S. Appl. No. 12/702,033, Notice of Allowance, Aug. 30, 2012.
PCT/US11/23886, International Preliminary Report on Patentability, Aug. 14, 2012.
PCT/US11/23886, International Search Report, Nov. 1, 2011.
PCT/US11/23886, Written Opinion, Nov. 1, 2011.

\* cited by examiner

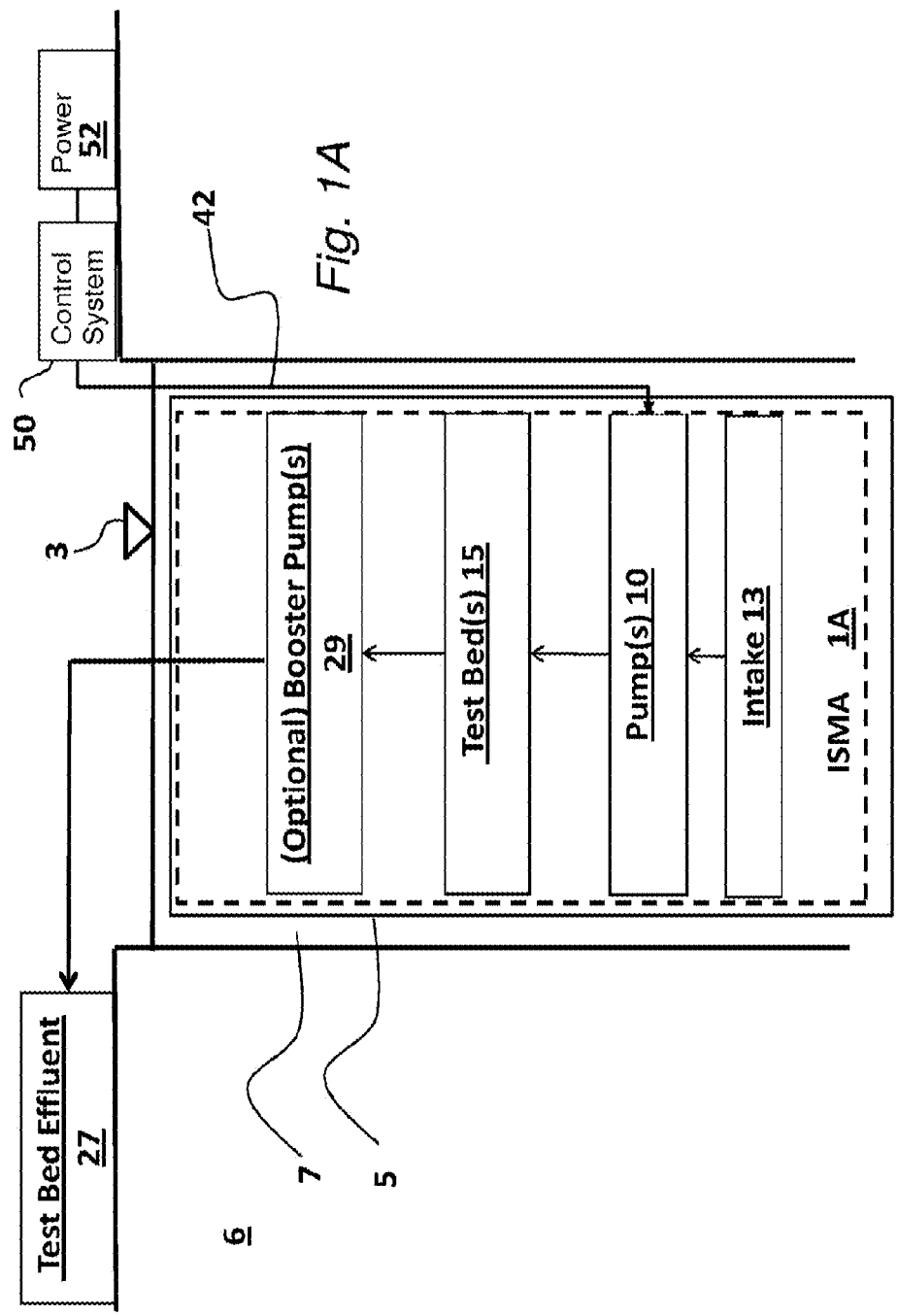

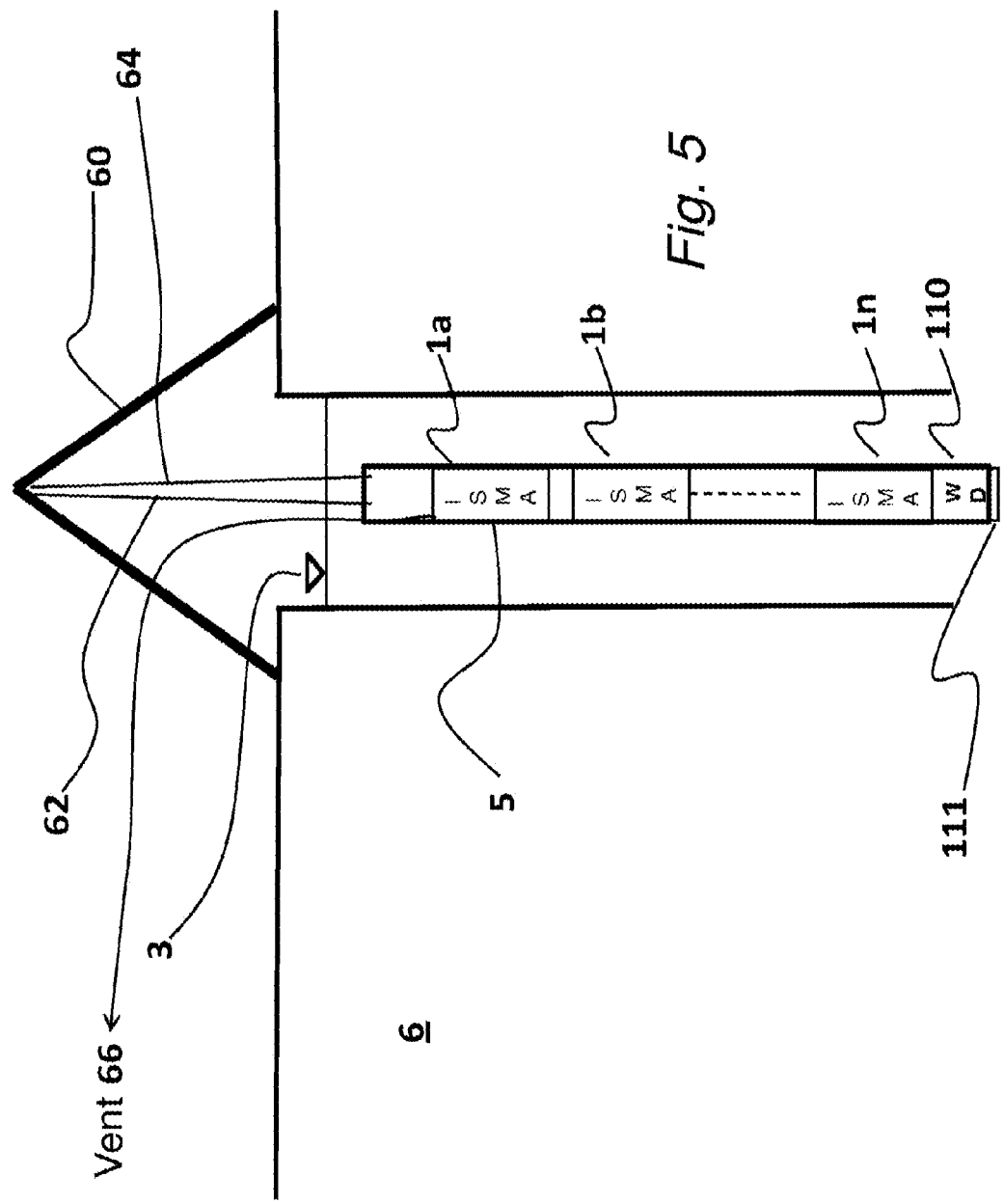

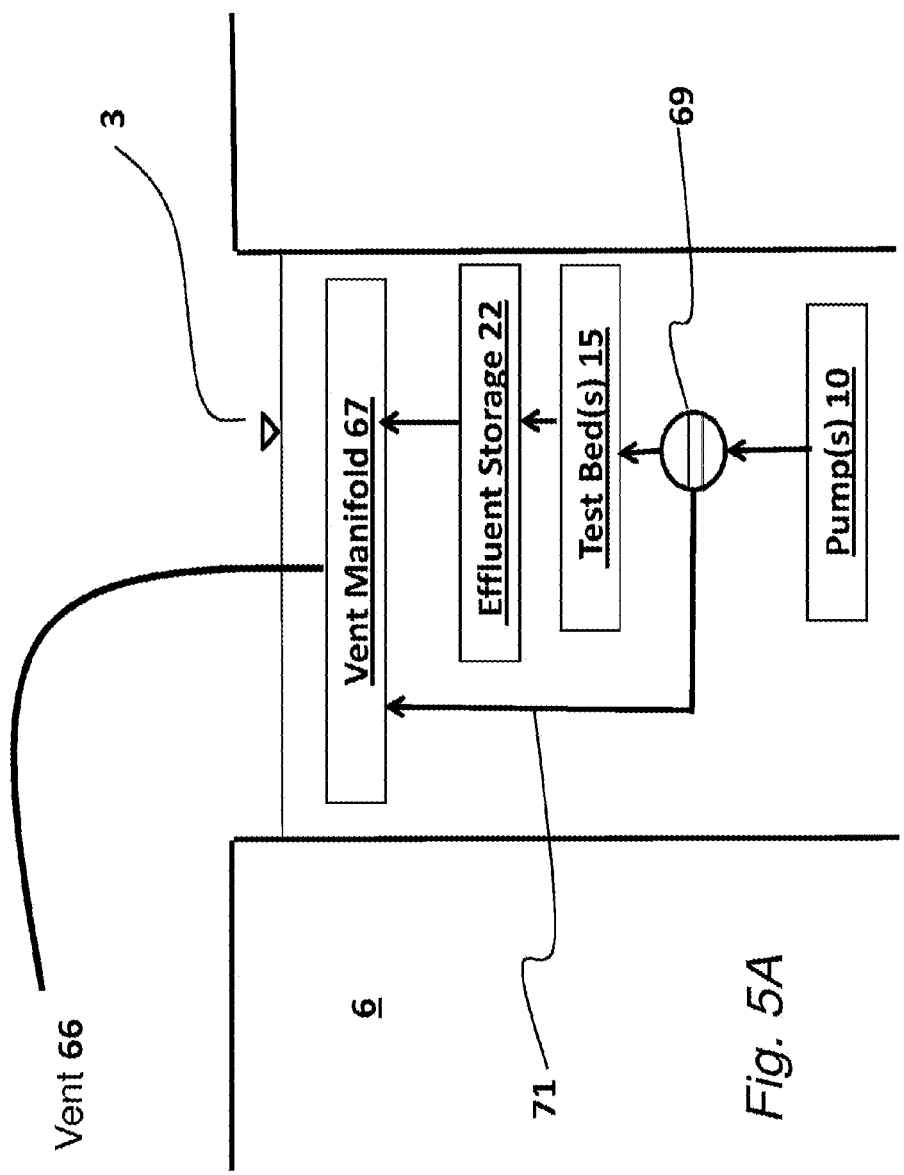

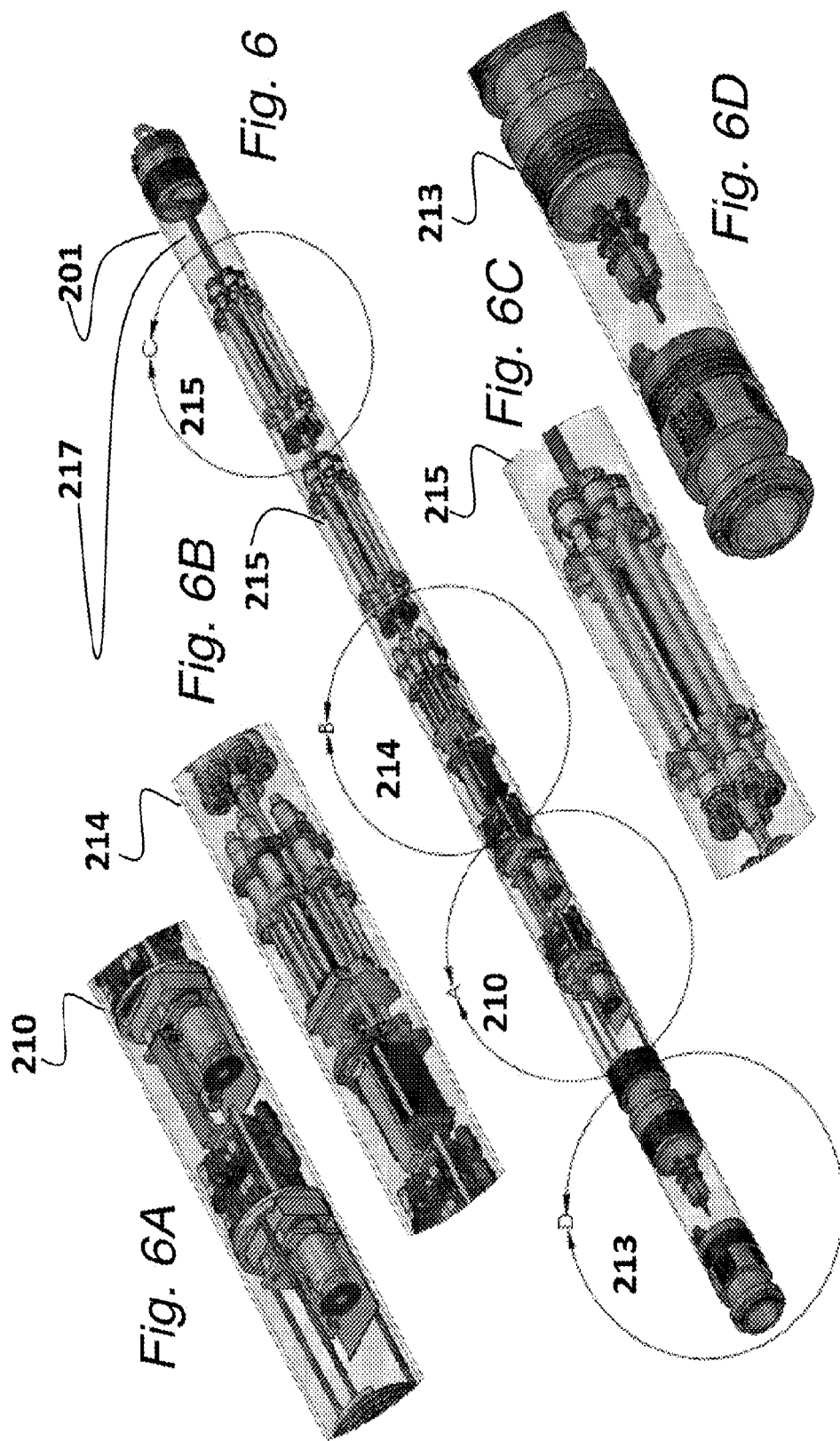

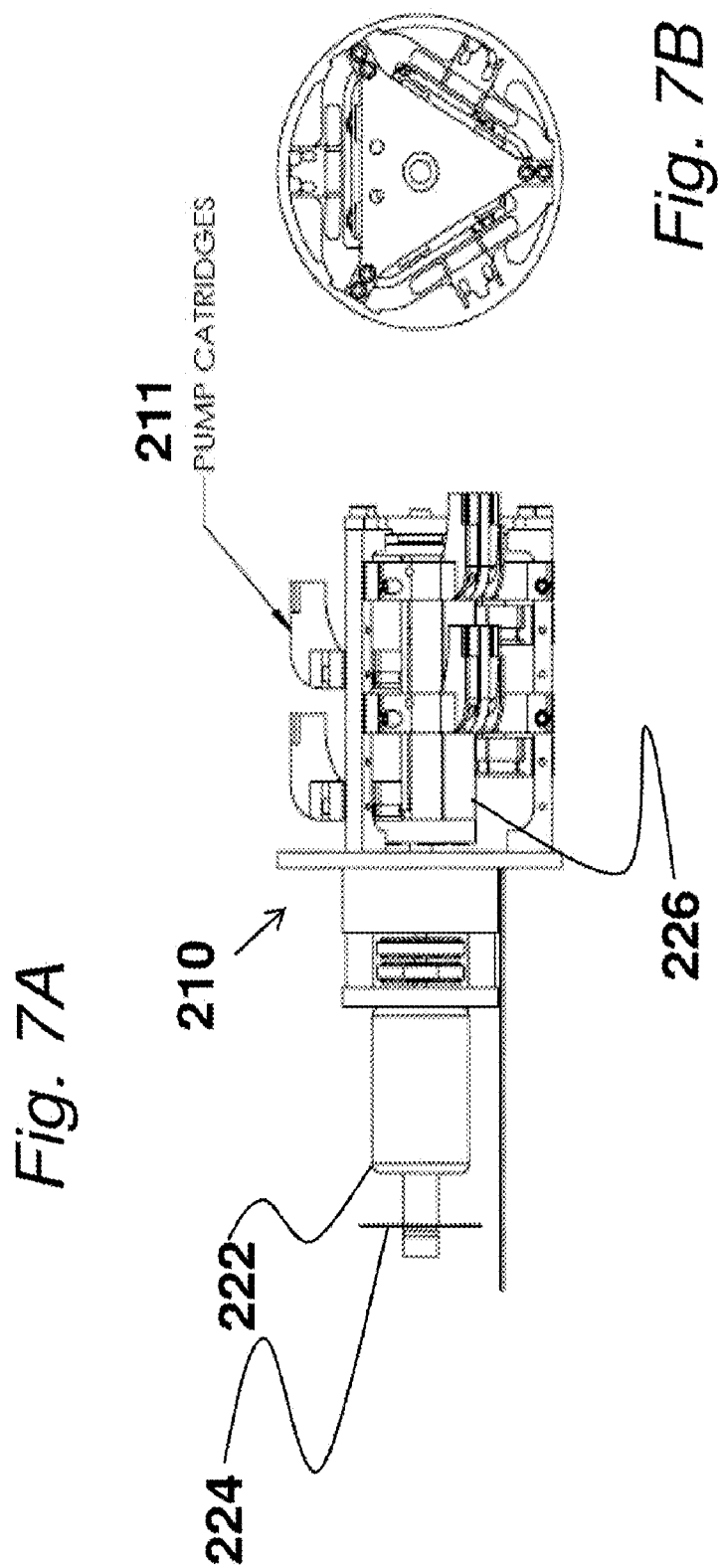

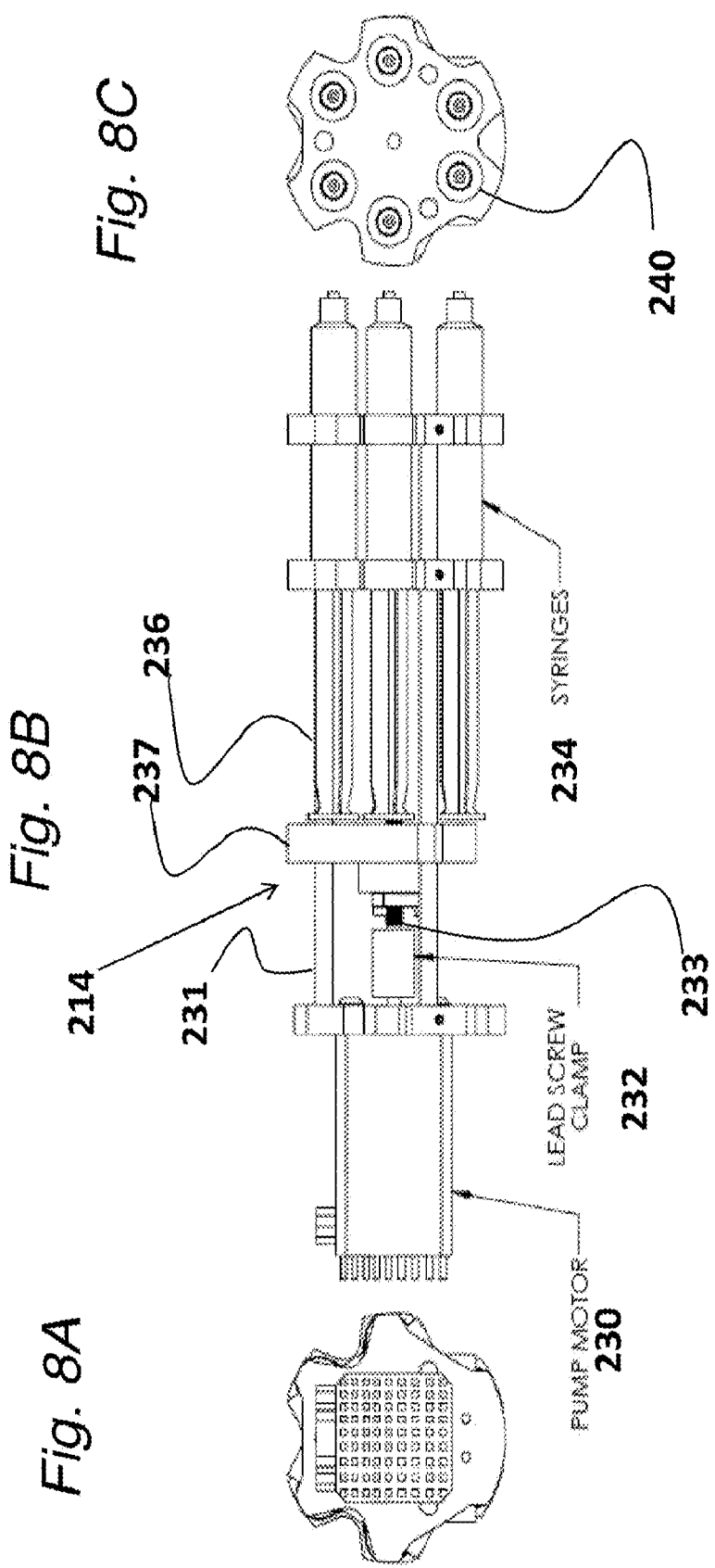

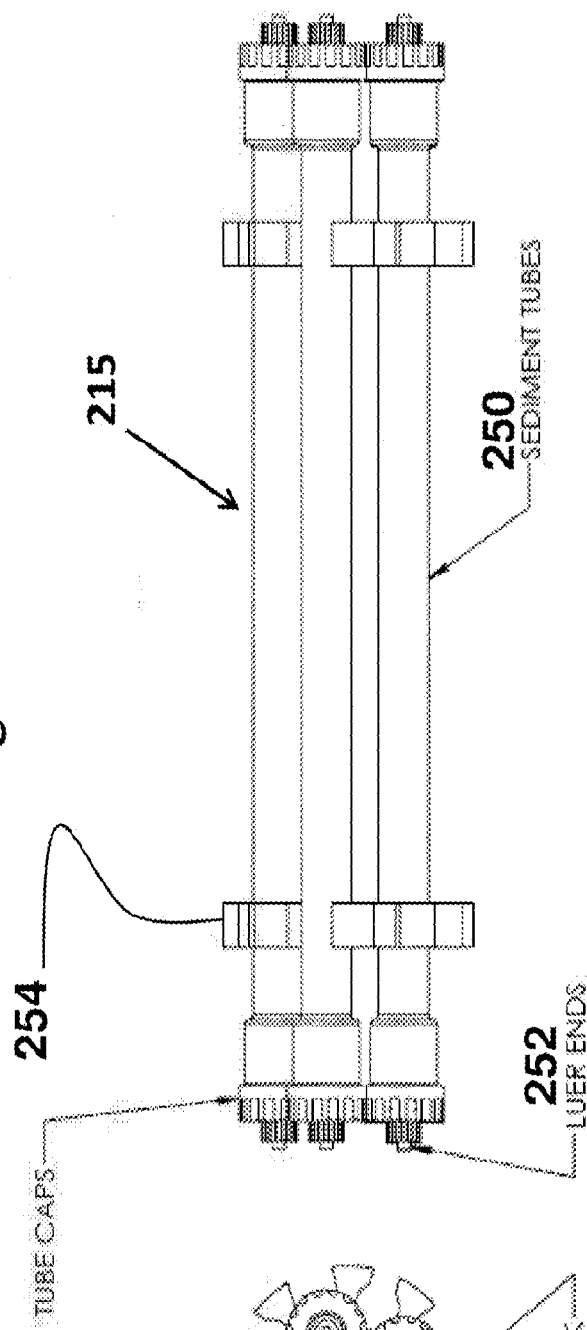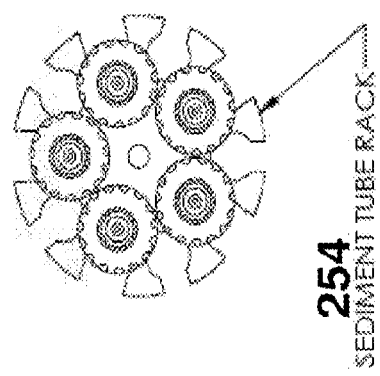

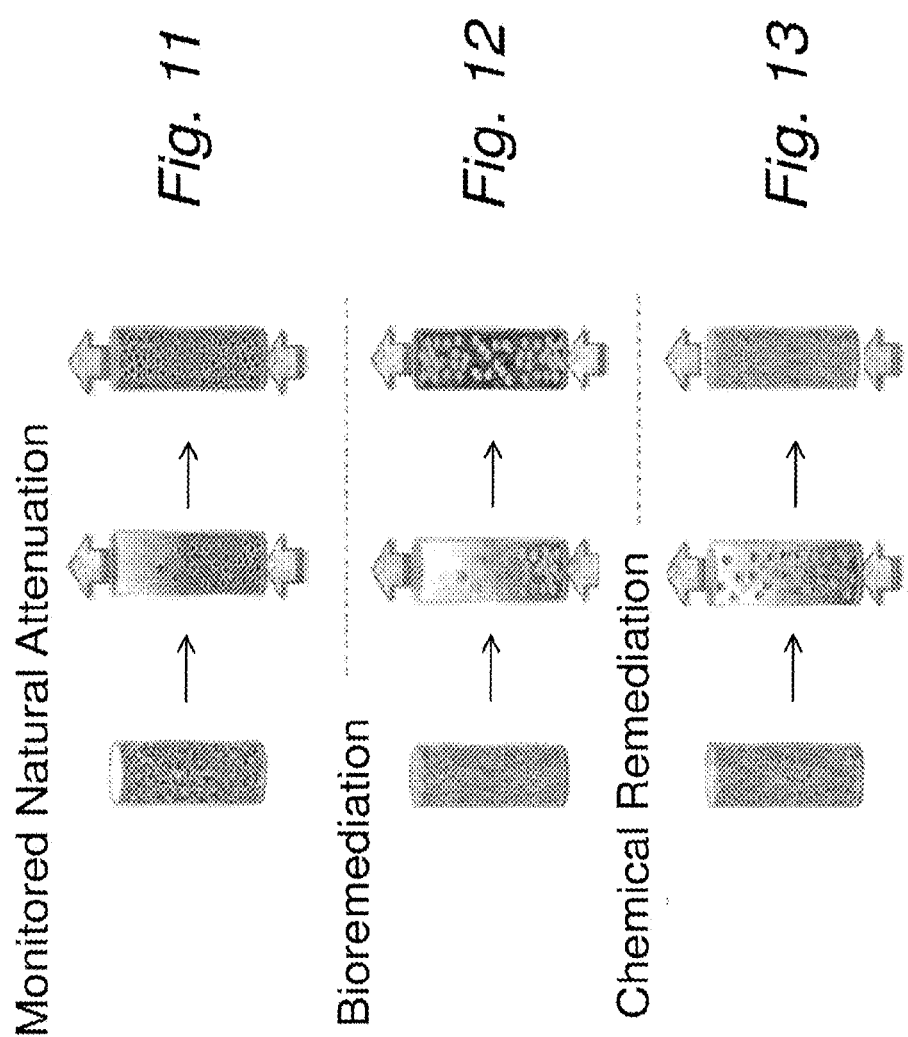

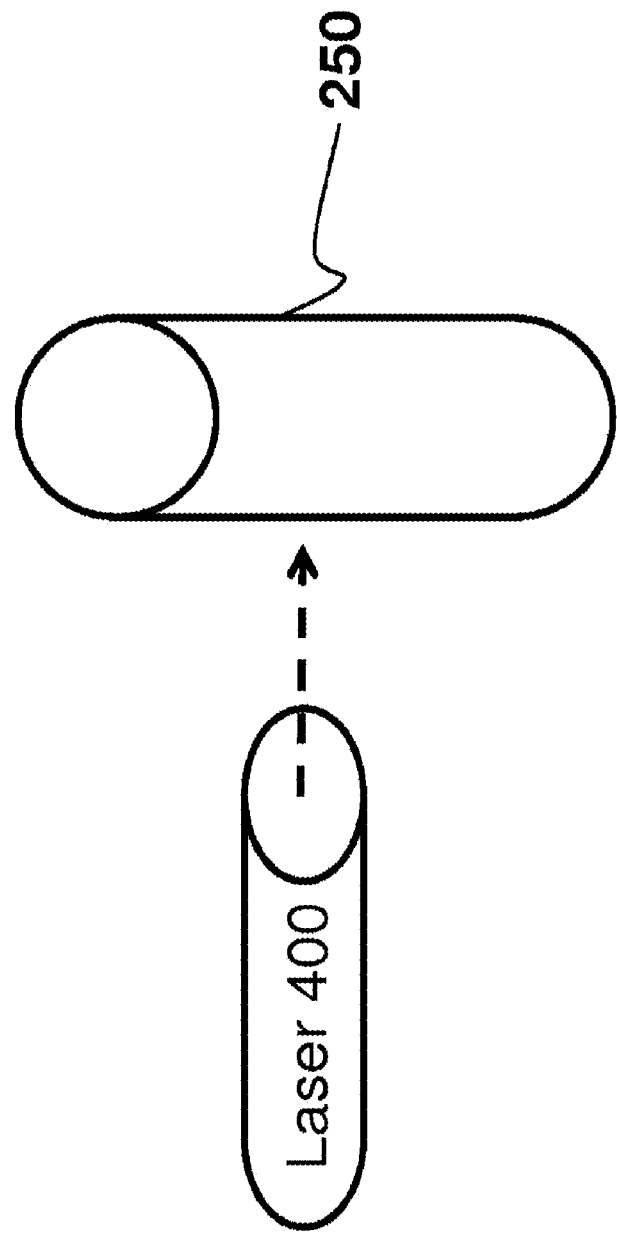

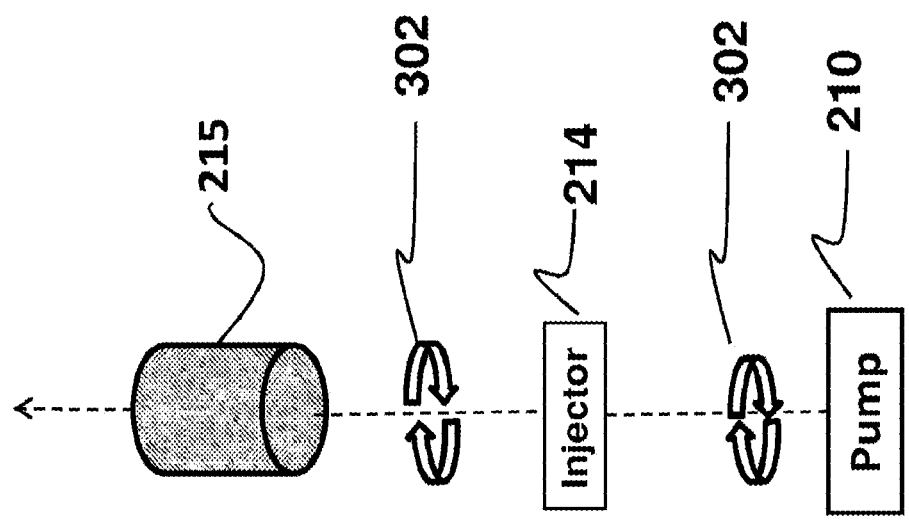

METHODS AND SYSTEMS FOR FLUID EXAMINATION AND REMEDIATION

CROSS-REFERENCE TO RELATED APPLICATIONS

This is a divisional application of U.S. application Ser. No. 12/702,033, filed Mar. 8, 2010 issued on Dec. 25, 2012 as U.S. Pat. No. 8,338,182, entitled "Methods and Systems for Fluid Examination and Remediation," and claims the benefit of the priority of that patent. U.S. Pat. No. 8,338,182 is incorporated herein by reference.

GOVERNMENT INTEREST STATEMENT

This invention was made with Government support under Contract DoD ESTCP ER-200914 awarded by the United States Department of Defense and Contract NIEHS-R01 1R01ES015445 awarded by the United States National Institute of Health. The Government has certain rights in the invention.

TECHNICAL FIELD

The present invention relates to measuring and testing of environmental and engineered phenomena including biological, chemical and physical processes. More particularly, the present invention relates to methods and systems for environmental remediation, monitoring, risk assessment and bioprospecting.

BACKGROUND

In situ bioremediation holds great promise as a safe and cost-effective strategy for cleanup of contaminated sediments and groundwater. The design of bioremediation systems requires site-specific characterization of the types of microorganisms present, what their potential metabolic capabilities are, and to what extent degradative functions are being expressed. The interactions between microbial communities and hazardous wastes also need to be assessed because while microorganisms frequently control both the rate and extent of contaminant degradation in the subsurface, contaminant mixtures and/or individual mixture components can affect the composition and activity of microbial communities indigenous to contaminated environments.

Laboratory batch and column experiments provide some information about pollutant/microorganism interactions, but cannot reproduce field conditions such as ambient water chemistry, aquifer temperature and the composition of natural microbial communities. Small-scale pilot tests conducted in the field provide better data, but carry the risk of impacting expensive monitoring wells and irretrievably introducing chemical and biological agents into the groundwater.

Previously, capillary microcosms were designed to capture, monitor, and enrich microorganisms in their natural habitat. The device, which can be deployed in a groundwater monitoring well, contains multiple flow-through column microcosms that are packed with site sediment and can be amended with chemical substrates and microorganisms to mimic biostimulation and bioaugmentation treatment approaches. As ambient groundwater is drawn through the capillary microcosms, resident microorganisms are allowed to interact with chemical and biological amendments. All water entering the device is stored in a single effluent container to prevent release of substances into the monitoring well and to enable the calculation of mass balances and biotransformation rates. Upon retrieval of the device from the well, site-specific information becomes available on the effectiveness of each of the treatment strategies tested. Following retrieval from a well, microorganisms are extracted for enumeration and characterization.

Previous methods are described in pending and allowed U.S. patent application Ser. No. 10/797,713, filed Mar. 10, 2004 and entitled "Method and Apparatus for Environmental Monitoring and Bioprospecting," to the same inventor as the present invention. U.S. patent application Ser. No. 10/797,713 is incorporated herein by reference. The prior method includes the steps of: (a) locating a sampling device in an environment to be investigated, wherein the prior device includes: (i) a container having a fluid inlet and outlet, (ii) a plurality of capillary microcosms situated within the container, each of these capillaries having an inlet and outlet that are configured so as to allow for fluid flow through the capillaries, each of these capillaries further having a means for covering its inlet and outlet so as to prevent flow through the capillary, (iii) a pump connected to the container inlet, the pump being configured so as to draw fluid from the surrounding environment, following which it is forced into the containers inlet and through the capillaries, (iv) connected to the outlet of the container, a means for collecting the flow forced through the capillaries by the pump, and (v) a check valve connected downstream of the container to prevent the backflow of fluid into the container, this plurality of capillaries being configured so as to allow for automated analysis of the capillaries using commercially available robotics, (b) opening the capillary covering means so as to allow fluid from the surrounding environment to flow through the container and capillaries, (c) leaving the device in situ for a temporal duration termed incubation period sufficient to study phenomena occurring within the capillary microcosms, (d) retrieving the testing device, and (e) analyzing phenomena occurring within the capillary microcosms using real-time sensors, automated analysis schemes and commercially available robotics.

Unfortunately, such known methods suffer from several drawbacks. For example, because the pumps are configured to draw fluid through the sampling device it is difficult to adequately pump sufficient samples through multiple microcosm units. A further drawback is that a single pump is used to draw water through all microcosm units, which may lead to uneven pressure displacement throughout the sampling unit and undesirable stop-flow conditions. Further, known units require the use of controlled valves for each microcosm capillary, which increases complexity.

The present invention provides a system that addresses and solves the aforementioned inadequacies, while providing a flexible and cost effective sampling system with additional features. For example, in previous designs cross-communication between microcosms was not possible, while the present invention using a modular design can easily accommodate experiments or tests requiring cross-communication between test beds, where a test bed comprises a sediment-filled glass column, for example. Other benefits and advantages of the present invention will become apparent from the disclosure, claims and drawings herein.

In a further advantage over known in situ microcosm array (ISMA) systems, the present invention allows effluent from each test bed to be collected separately. In addition, larger amounts of fluid may be collected, thereby allowing chemical analysis of fluid, such as, for example, groundwater at heretofore unachievable, low detection limits. Known systems allowed for analysis of capillary content but not analysis of the effluent collected individually from each test bed.

BRIEF SUMMARY OF THE DISCLOSURE

A method for in situ monitoring within a specified environment. The method includes locating a housing in a well, wherein a set of pumps and a plurality of test beds are inserted. Each of the set of pumps are controlled by signals from the control system to push water from each pump into one of the plurality of separate test beds where, after flowing through each of the test beds, effluent flows into an effluent storage device.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 1A schematically shows an alternative embodiment of an ISMA assembly.

FIG. 5 schematically shows an example of a mounting arrangement for a plurality of in situ microcosm array assemblies positioned in a groundwater well.

FIG. 5A schematically shows an example of a venting arrangement for an in situ microcosm array system positioned in a groundwater well.

FIG. 6 with inserted FIGS. 6A-D schematically shows an example of test components employed in an example embodiment of a system for in situ monitoring, analyzing, risk assessment, and bioprospecting.

FIG. 7A-FIG. 7B schematically show an example of a plurality of pumps arranged for good space economy and employed in an example embodiment of a system for in situ monitoring, analyzing, risk assessment, and bioprospecting.

FIG. 8A-FIG. 8C schematically show an example of an optional injection module employed in an example embodiment of a system for in situ monitoring, analyzing, risk assessment, and bioprospecting.

FIG. 9A-FIG. 9B schematically show an example of a test bed module employed in an example embodiment of a system for in situ monitoring, analyzing, risk assessment, and bioprospecting.

FIG. 11 schematically shows an example of a test bed used for assessing monitored natural attentuation.

FIG. 12 schematically shows an example of a test bed used for assessing a bioremediation process.

FIG. 13 schematically shows an example of a test bed used for assessing a chemical remediation process.

FIG. 14 schematically shows an example of a test bed used for assessing a physical remediation process.

FIG. 16 schematically shows an example of a swivel joint between modules employed to prevent the unit from getting lodged in a well.

Figure 1:
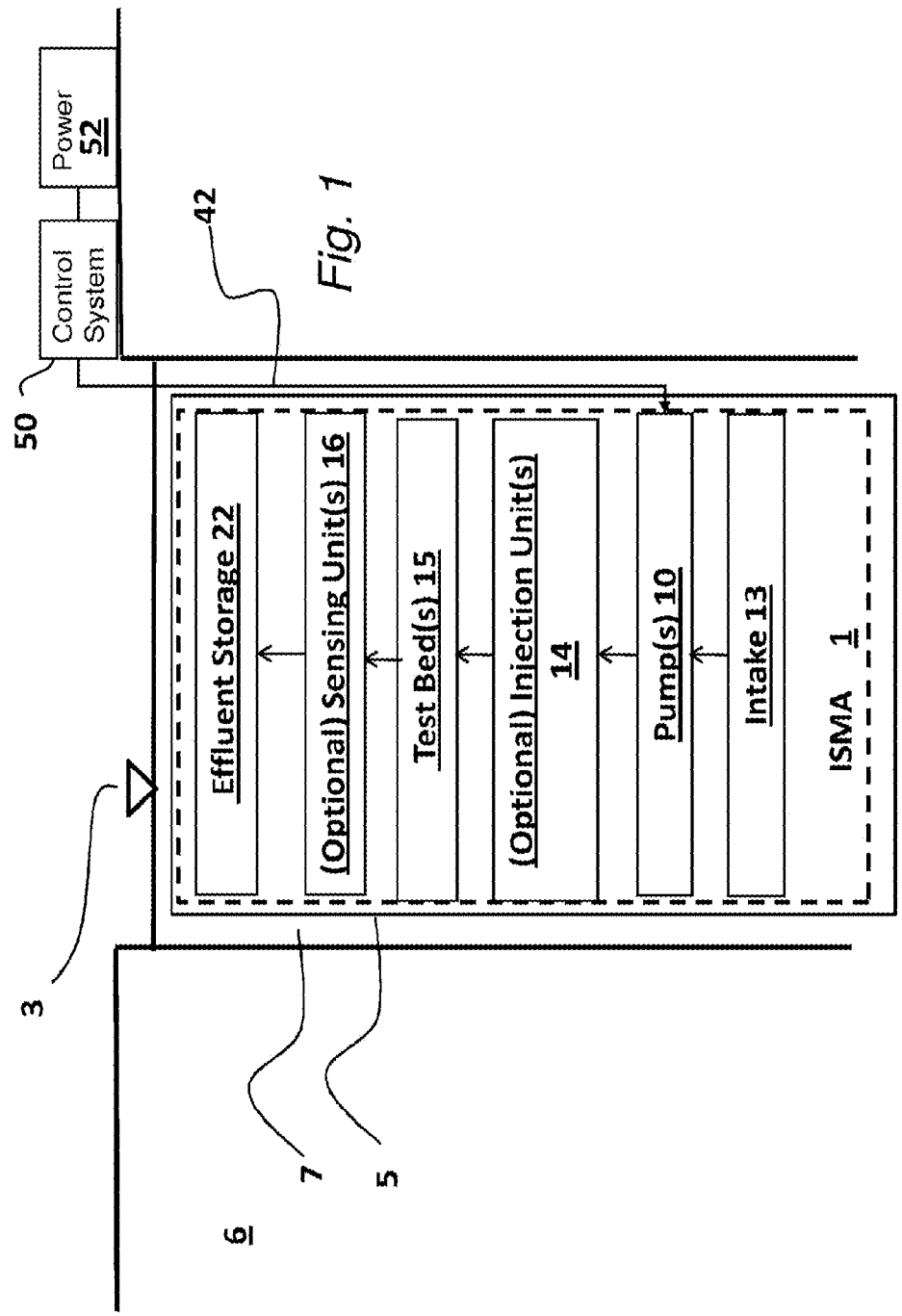
FIG. 1 schematically shows an example embodiment of a system for in situ monitoring, analyzing, risk assessment and bioprospecting within a specified environment.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE PREFERRED EMBODIMENTS

The following disclosure describes several embodiments and systems for a system for in situ monitoring, analyzing, risk assessment, and bioprospecting within a fluid environment. Several features of methods and systems in accordance with example embodiments are set forth and described in the Figures. It will be appreciated that methods and systems in accordance with other example embodiments can include additional procedures or features different than those shown in the Figures. Example embodiments are described herein with respect to wells. However, it will be understood that these examples are for the purpose of illustrating the principles, and that the invention is not so limited.

Additionally, methods and systems in accordance with several example embodiments may not include all of the features shown in these Figures. Throughout the Figures, identical reference numbers refer to similar or identical components or procedures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or various combinations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Referring now to FIG. 1, an example embodiment of a system for in situ monitoring, analyzing and bioprospecting within a specified environment is schematically shown. An in situ microcosm array assembly (ISMA) 1 is located in a tubular housing 5 placed into a well 7, where the well has been drilled or otherwise bored into the earth 6. The ISMA 1 is lowered into the well 7 and positioned below the water line as indicated by marker 3. The ISMA 1 includes an intake 13, at least one pump 10, at least one test bed 15 and at least one effluent storage device 22. As used herein the term "test bed"

generally refers to a unitary flow-through container holding materials used for testing purposes, such as, for example, a sediment column or the like.

The at least one pump 10 may include at least one pump channel and may advantageously be controlled by a control system 50 located in one embodiment on the ground surface and in communication with the ISMA as generally indicated by control line 42 and powered by a power system 52. The power system 52 may include any power setup useful for remote locations such as battery power, solar power, transmission line supplied power or the like. Using independent power generation from solar panels, storage batteries and equivalent devices, the unit may be operated off the grid with DC current provided for "around-the-clock" operation, day and night. Note that, as explained below, due to the modular design of the ISMA 1, the intake 13 and any of the other components may be arranged in any suitable arrangement within the ISMA assembly 1 (delineated by the dashed line in FIG. 1) and with respect to each other.

The ISMA assembly 1 may optionally include at least one injection unit 14. The ISMA assembly may also optionally include at least one sensing unit 16. If included, the sensing unit 16 may advantageously be coupled to receive fluid flowing from one or more of the at least one test beds 15 or from tubes that bypass the test beds and thus are representative of the composition of the liquid drawn into 1 from the surrounding environment. After processing in the sensing unit 16, the fluid is stored in effluent storage device 22. The effluent storage device 22 may comprise a plurality of plastic bags, bladders or the like, where fluid flowing through the test beds and downstream components is stored. Venting of gasses from the storage device may be achieved by inclusion of a bleed valve using, for example, tubing rising along the primary cable to a location some distance above the fluid intake. As the fluid flows through the ISMA assembly, microorganisms and chemicals can be trapped in the test beds 15. The ISMA assembly 1 can be removed from the environment for further analysis immediately after a cycle of pumping or after a prolonged incubation period. In one useful embodiment, described further below, the intake 13 may comprise a generally tubular water pickup having multiple intakes located around its peripheral surface in fluid communication with the at least one pump 10.

All materials are corrosion resistant, e.g., stainless steel, Teflon® material (i.e. polytetrafluoroethylene) or the like. In addition, all materials have limited sorption capacity for analytes of interest such that liquid components of interest are not accumulating on material surfaces presented. Furthermore, exposure of metal surfaces is limited or can be completely avoided by coating metallic parts with a suitable coating made out of, for example, Teflon® material. Real-time and monitoring equipment can be added to a sampling array to increase functionality and to trigger reactions at specific points in time selected by changes in the target environment (e.g., heavy rainfall events). Use of radio frequency signaling and remote controls can replace communication cables. The monitoring equipment may advantageously include detectors for monitoring properties such as acidity (pH), oxidation/reduction potential (Eh), dissolved oxygen (DO), ion-specific electrodes and chemical sensors.

Referring now to FIG. 1A, an alternative embodiment of an ISMA assembly is schematically shown. A modified ISMA assembly 1A includes at least one optional booster pump 29 that may be employed to transfer effluent from the various test beds 15 separately from the subsurface deployment location to an above ground container 27. Transfer of effluent to the ground surface allows for the device to become very compact as it eliminates the need for storage of liquids in the borehole. Since space is essentially unlimited above ground, the unit can be operated essentially indefinitely in situ. This enables the performance of long-term deployment tests that would mimic long-term performance of tested technologies. This is particularly important for processes that have long adaptation times such as the cultivation of anaerobic microorganism in formerly aerobic groundwater. Note that the ISMA, in this preferred embodiment, is operated as an upflow system to allow for gas bubbles to rise and exit the test beds rather than becoming entrapped.

Figure 2:
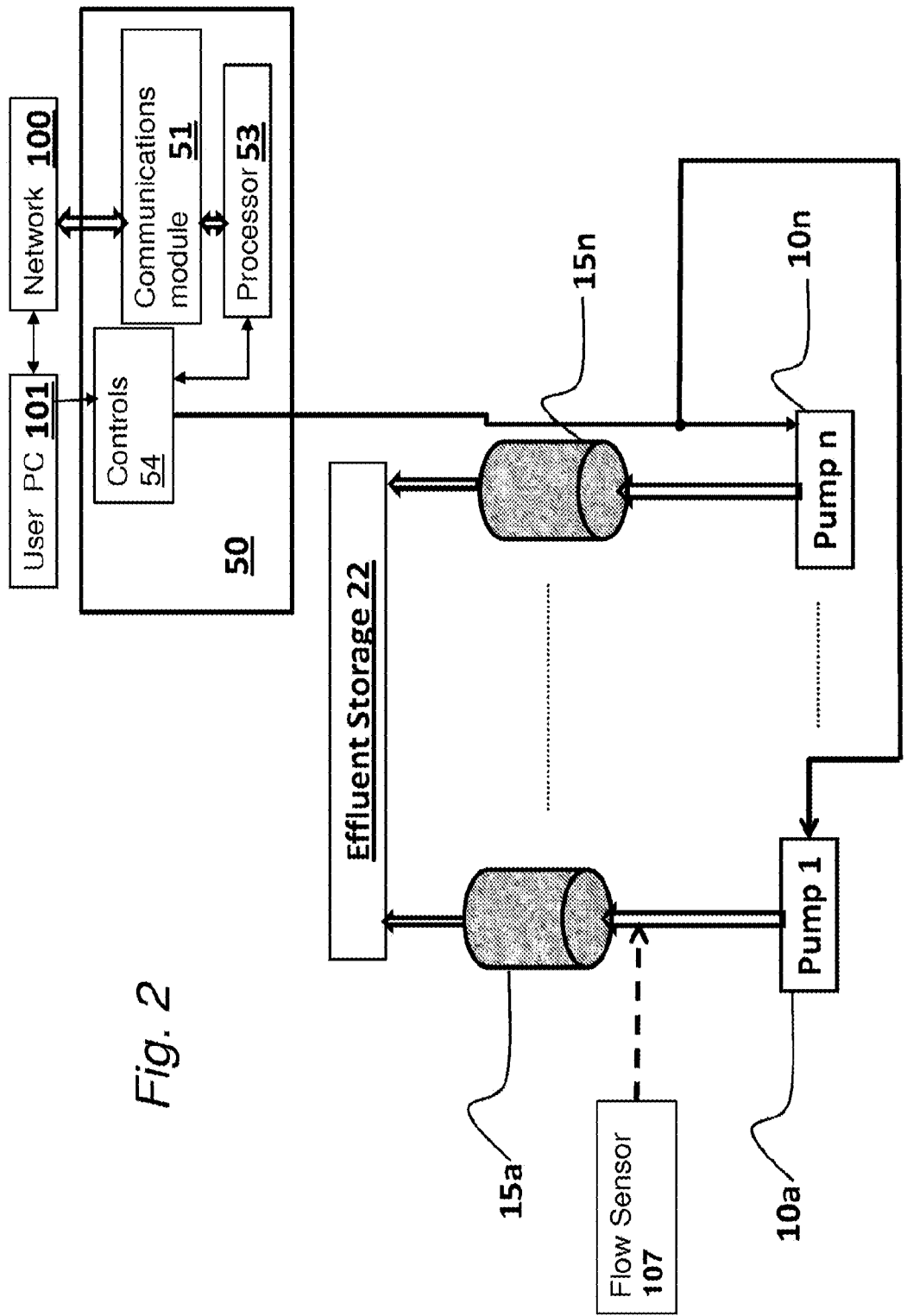
FIG. 2 schematically shows one example configuration of the system of FIG. 1.

Referring now to FIG. 2, one example configuration of the system introduced in FIG. 1 is schematically shown. A set of pumps including Pump 1 through Pump n $10a$-$10n$ are inserted into an ISMA assembly. Here "n" is understood to be an integer representing a plurality of pumps. Water is pushed from each pump into one of a plurality of test beds $15a$-$15n$ and, as an option, through tubing that bypasses the test beds. Water bypassing the test beds 15 and collected separately in the effluent storage 22 can inform, via real-time or lab analysis, on the composition of the liquid drawn into the container 1 from the surrounding environment. After flowing through the pumps the water from each of the test beds $15a$-$15n$ flows into the effluent storage device 22. Each pump $10a$-$10n$ is controlled by signals from the control system 50. In one example the control system 50 may include controls 54 coupled to activate, de-activate and/or otherwise control the rate of flow pushed into the test beds by each pump. Also included in the control system 50 may be a processor 53 and a communications module 51, for example. The controls 54 may, in turn, receive operating signals from the processor 53 or directly from a user operating a personal computer 101 or the like either remotely or on site. In some embodiments, flow sensors 107 can be integrated in various locations throughout the ISMA system.

Figure 3:
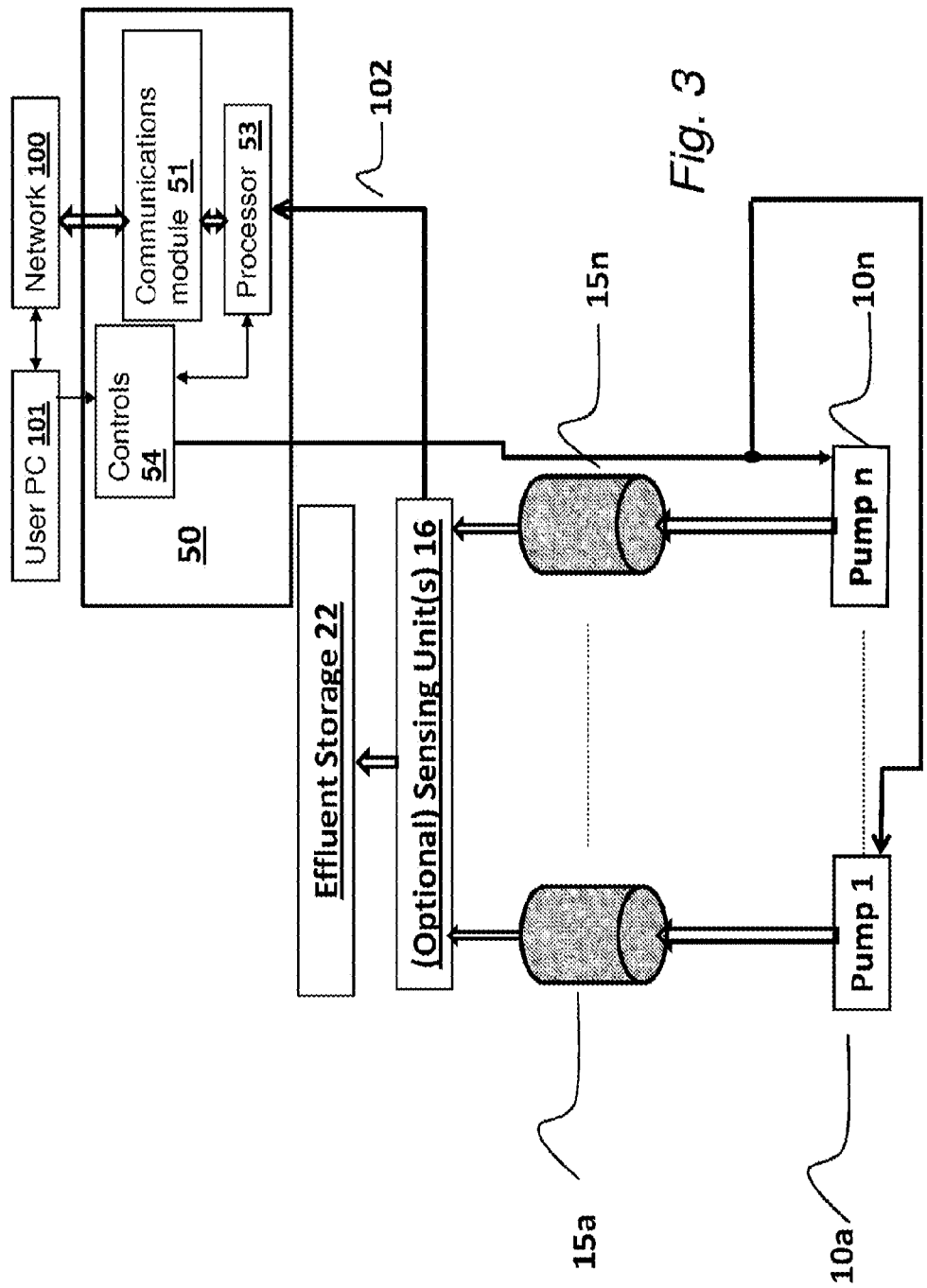
FIG. 3 schematically shows an alternate example of devices used in the system of FIG. 1.

Referring now to FIG. 3, another example configuration of the system first introduced in FIG. 1 is schematically shown. The configuration includes a plurality of pumps $10a$-$10n$ which operate as described above, but here one or more optional sensing units 16 are disposed to receive the outflow from a plurality of test beds $15a$-$15n$. The optional sensing units integrated into the ISMA assembly comprise sensors selected to detect predetermined parameters in the water flowing through the test beds. An output signal line 102 is coupled to communicate with, for example, the processor 53. The processor 53, in turn may communicate received sensor information to a network 100, such as a private network, WAN, LAN or Internet through communications module 51. A user may receive the information for review and processing at user PC 101, where the user PC is a personal computer or equivalent. Effluent from the sensors is then stored in effluent storage reserves 22.

Figure 4:
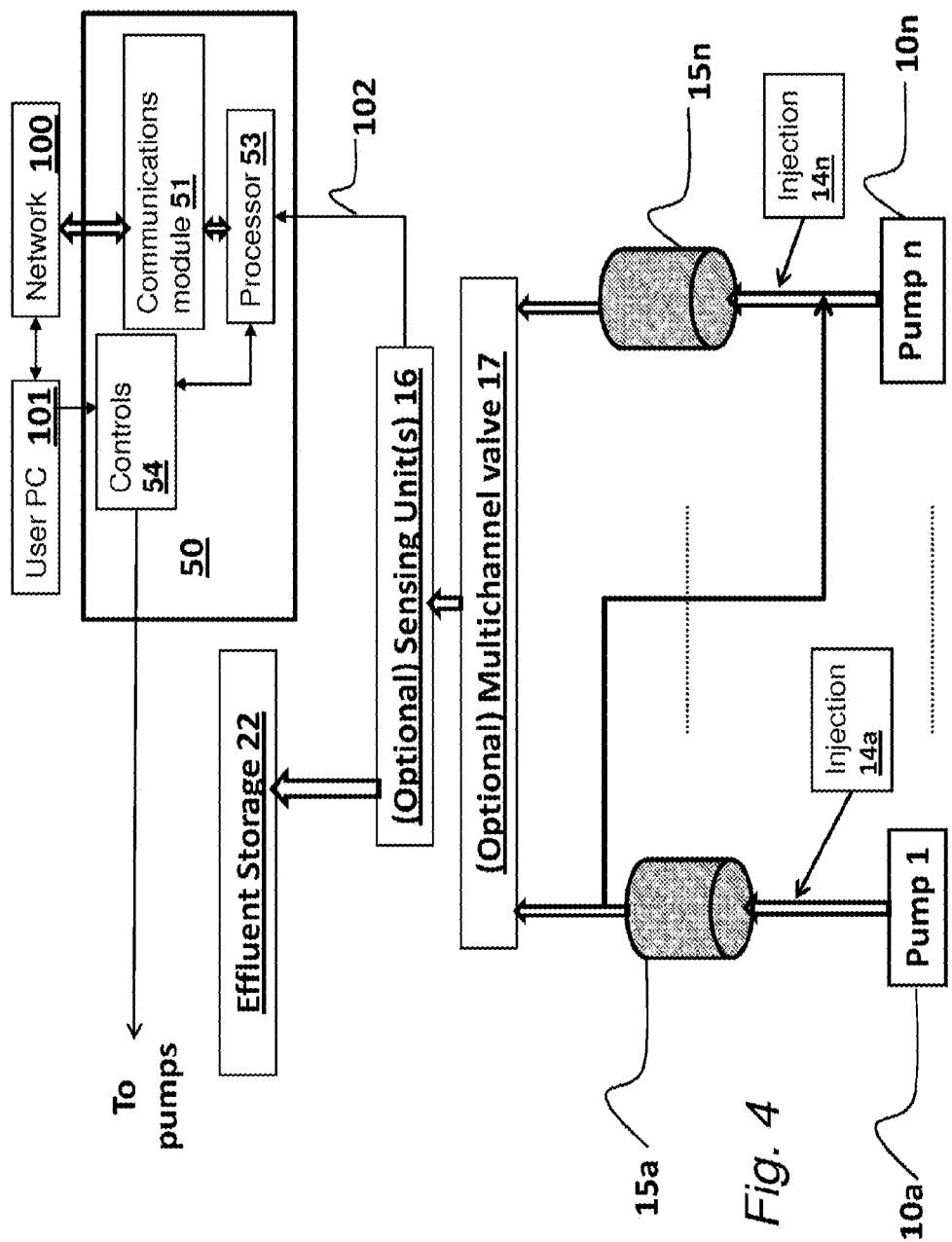
FIG. 4 schematically shows another alternate example system for in situ monitoring, analyzing, risk assessment and bioprospecting.

Referring now to FIG. 4, another example configuration of the system first introduced in FIG. 1 is schematically shown. A plurality of pumps $10a$-$10n$ and one or more optional sensing units 16 are disposed to receive the outflow from a plurality of test beds $15a$-$15n$. The system here operates substantially similarly to that of FIG. 3, but additionally features at least one optional multichannel valve 17 interposed between the test beds and the sensing units. The at least one optional multichannel valve controls fluid flow downstream of the plurality of test beds 15 to the sensing units so as to allow fluid from selected test beds to flow into the sensing units 16 at any point in time. Thus fluid flowing to the sensing units can be restricted to fluid from a single test bed for analysis as desired. The at least one multichannel valve may be operated by the controls 54, processor 53 or other conventional controllers. One or more injection units 14a-14n may be added to inject material, including but not limited to chemicals or biological material into the fluid flowing into any one or all of the test beds, depending on the application desired. In this way chemical treatment of materials can be carried out by the system. Injection module(s) and sensing module(s) may, but do not have to, be present in the same device.

The modular design allows for operation of test beds in series to enable turning aerobic groundwater into anaerobic groundwater, which is then fed into a test bed fitted, for example, with strict anaerobic bacteria that do not tolerate any oxygen. In this configuration, the effluent of one column becomes the influent of another column. The configuration can be changed through switching valves controlled from the ground surface via an umbilical signal cable or remotely through a signal sent to a receiver station located above ground at the deployment location. In said configuration, the benefit of the sensing unit is readily apparent, as it enables the determination of the proper time to switch the effluent of one test bed to make it the influent of another test bed. In the case of testing of strict anaerobic bacteria in formerly oxygenated groundwater, premature switching of effluent to the bioaugmented test bed would immediately and permanently inactivate all strict anaerobic microorganisms. Similar benefits are reaped when operating a test bed with an oxygen sensitive catalytic material, for example. In addition, multiple test bed columns may be run in series to achieve longer hydraulic residence times.

Referring now to FIG. 5, an example of a mounting arrangement for a plurality of in situ microcosm array assemblies positioned in a groundwater well is schematically shown. A housing 5 contains a plurality of ISMA assemblies 1a-1n, wherein, for example, each ISMA assembly may comprise a different set of test bed configurations and compositions. The housing 5 is held in place by a support structure 60, where the support structure 60, such as, for example, a tripod, is attached to the housing 5 by, for example, a main support cable 62. For safety, a tether 64 may also be attached to the housing 5. At least one vent 66 may be inserted into the housing and/or ISMA assemblies to release potentially dangerous vapors and to prevent air locks in the system.

The main support cable and tether provide two means of securing an ISMA unit in and retrieving the unit from the subsurface. In one embodiment, an eye bolt to which a (e.g., steel) cable can be attached is mounted at the upper end of the unit. In addition, the new design features the tether 64 that serves as a secondary holding mechanism. Should the unit become unhinged from the eye bolt due to mechanical problems or operator error, the tether 64 would operate as a safety cable that prevents the unit from falling into the bore hole.

Water sensors may be built into the unit to detect the existence of leaks in the system. When the sensor detects a leak, the information is sent to the control system at the surface and communicated to the operator, who then can take appropriate action, such as a remote shut-down of the unit to protect electronic components from flooding. When multiple units are deployed in the same area or plume, individual units may be shut down in sequence when real-time sensors indicate termination of the experiment is warranted. Then, when the last ISMA unit has ceased to operate, all units can be retrieved in a single field campaign to maximize productivity and reduce costs from fieldwork. Water detection sensors WD 110 may be used to determine depth of submersion of the unit. For most experiments, it is desirable to fully submerse the unit so that it assumes the temperature of the groundwater of interest. Also, submersion insures that the intake is below the water table and thus water is available to the internal pumps. Flow sensors may advantageously be integrated in various locations in the device to inform whether the experiments in the separate test beds are proceeding as planned or whether technical difficulties exist such as clogging or pump failures.

An easy-drain bottom cap 111 may be included, as well as an optional sump pump for pumping water up and out of the well in a fault tolerant design. The bottom cap 111 may be equipped with a drain bolt. When sensors indicate that the unit is flooded, the whole unit can be retrieved with a crane from the borehole, the drain plug will be removed, and the water that has accumulated in the unit can safely be drained into a hazardous waste drum without risking spillage of contaminated water to the ground or into the well. In addition, a sump pump can be included that can pump excess water up and out of the well to safeguard the electronic equipment, sensors and pumps within the unit. Protective structures or "umbrellas" can also be integrated in the design so that if there is a leak above sensitive equipment (such as the pump modules), the water will run past the pumps without dripping on top of them and harming the electronics.

Referring now to FIG. 5A an example of a venting configuration is schematically shown. Proper venting is important to prevent explosive gases to build up and create an explosive mixture. Provisions have been made to vent gases from the ISMA assembly through a vent line to the ground surface and atmosphere to prevent hazardous conditions and the possibility of explosions.

Effluent condensation and gas venting can be managed with a conventional condensate trap to prevent vent lines from clogging or becoming water logged. In one embodiment an electric air pump may be employed for continuously adding fresh air in order to prevent an explosive mixture from building up in the well. A manifold 67 may be coupled to the effluent storage bags 22 to vent excess air. The same or a different manifold may be coupled by tubes 71 to air bleed valves 69 that may advantageously be located in front of test beds 15 to allow for use of wet sediment columns. Air trapped between a pump 10 and a test bed 15 can be safely vented out of the lines using the air bleed valve 69. If air is not vented, air bubbles can result in clogging of the sediment columns and stoppage of flow. The air bleed valves may be controlled remotely using the processor and control system.

Referring now to FIG. 6, an example of a modular ISMA assembly is schematically shown. A modular ISMA assembly 201 includes an intake module 213, a pump module 210, an injection module 214, and a set of test bed modules 215. Not shown is the effluent reservoir that may be located upstream of the test bed modules. For clarity's sake, not shown in this drawing are various cables, tubes and connectors that must be assembled prior to installation of the ISMA assembly into a well. However, it will be understood that fluid and electrical connections are made conventionally. The ISMA system features an internal frame 217 for easy access and assembly. Bayonet closure mechanisms, similar to those used on SLR cameras, may be effectively employed on the module ends for making quick, reliable connections between different modules. ACME threads or similar tread types can also be used to assemble components and modules as depicted in FIG. 6D.

FIG. 6A-FIG. 6D illustrate more details of the various modules. Note that in one useful embodiment, the modular design allows the various modules to be located within the ISMA assembly in any desired arrangement or combination of arrangements. Due to the modular design, it is possible to scale the system up or down depending on the size of the well. For example, by changing the diameter of the snap-in column holders holding in place the plurality of test beds, larger test beds can be accommodated and housed in a tubular external housing of larger diameter.

Referring now to FIG. 7A and FIG. 7B, a more detailed example of a pump module as used in an ISMA assembly is shown. With respect to FIG. 7A, a side view of a pump module 210 including a set of pump cartridges 211 is shown. Also included is a motor 222. In one useful embodiment the pump module 210 comprises a peristaltic pump wherein the motor 222 comprises a stepper motor including an encoder 224. In operation, the motor 222 drives a set of rollers 226 which cooperate with the pump cartridges to control fluid flow through the pump using peristaltic flow. This flow regime is advantageous as it prevents groundwater from ever contacting any of the pump components. Only the inexpensive, peristaltic tubing is being exposed to groundwater and the tubing is discarded after tests to prevent carryover from one deployment location to the next. More importantly, as a result, no valves are required to restrict or allow fluid to be pushed into the test beds. Each test bed in the ISMA assembly may advantageously be connected to a dedicated pump. FIG. 7B shows a top view of the pump module including the substantially circular profile designed to fit within the housing 5.

Referring now jointly to FIG. 8A, FIG. 8B and FIG. 8C, a bottom view, side view and top view of a detailed example of an injection module as used in an ISMA assembly is shown. The injection module 214 comprises a motor 230, such as a stepper motor or the like, a drive assembly 231, including a lead screw 233, a lead screw clamp 232, a plurality of syringes 234 including syringe plungers 236. A push plate 237 bears on the plungers 236. Luer connecters 240 may advantageously be used for connecting the syringe outputs to conduits running to fluid ports for injecting materials into the test beds. In operation the motor 230 drives the lead screw which pushes the push plate 237 against the plungers so as to force fluid out of the syringes 234, thereby injecting the contents into the test bed fluid input. In one useful embodiment the syringes may comprise 10 ml syringes. However, the size of the syringes and other components is a matter of design choice and may vary depending upon the application and environments being processed. The injection module can be configured to accept syringes of various sizes. In one preferred embodiment, the injection unit is configured to continuously feed a small quantity of chemical amendments to the plurality of test beds, thereby mimicking the environmental remediation method of biostimulation by continuous injection of chemical nutrients.

Referring now jointly to FIG. 9A and FIG. 9B, a side view and a top view of a detailed example of a test bed module as used in an ISMA assembly is shown. The test bed module 215 comprises a plurality of test beds 250, including end caps 252, where the test beds are joined by a set of snap-in column holders 254 for easy assembly or disassembly. The end caps may advantageously be Luer connecters 252 for connecting the test bed input ports and output ports to fluid pushed through from the pumps, including any injected material from the injection module, if used. The test beds 250 may advantageously be made from clear glass sediment tubes or the like to allow visual inspection of the tube contents when desired.

Figure 10:
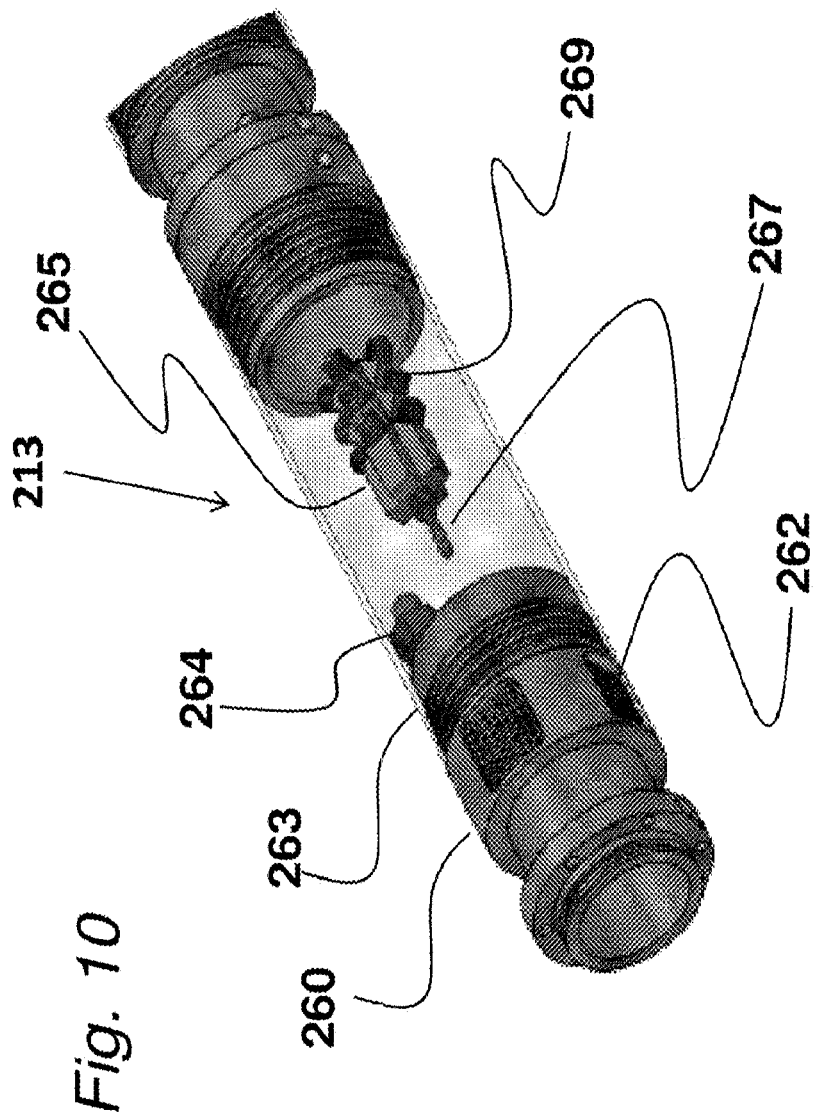
FIG. 10 schematically shows an example of a water intake and plurality of output ports employed in an example embodiment of a system for in situ monitoring, analyzing, risk assessment, and bioprospecting.

Referring now to FIG. 10, a detailed example of an intake module as used in an ISMA assembly is shown. The intake module 213 comprises a pickup element 260 having a plurality of intake ports 262 for receiving fluids from, for example, a groundwater environment from multiple directions. In one example there are four such intake ports. The intake ports may advantageously be fitted with a filter of a pore size suitable to allow microorganisms into the device but screening out larger sand particles that may lead to internal clogging of tubing and the test beds.

The module is assembled within a module housing, such as a stainless steel tube, using, for example, ACME style threading 263 to avoid cross threading problems. A manifold assembly 265, made with, for example, Delrin® brand thermoplastic material or the like is located downstream from the intake 260. The manifold assembly 265 includes an intake nozzle 267 and a plurality of output ports 269. A swivel outlet 264 is in fluid communication with the intake ports in order to deliver fluids from the environment to the manifold assembly 265. Note that throughout the figures required conduits and tubes have not been shown in the drawing in order to simplify the figures, but the required fluid connections will be understood by those skilled in the art. In practice, liquid passing through the pickup element 260, will be split in flow and diverted into separate lines of tubing by the manifold assembly 265 featuring the outputs 269 that will route fluid to the pumps which will push said fluid into the test beds.

Generally, swivel junctions may be used in fluid lines to allow for the free rotation of the ISMA modules relative to each other. Conventional quick-connectors may advantageously be used for making tubing connections. As shown in FIG. 16, a swivel joint 302 between modules may be employed to prevent the unit from getting lodged in a well.

In a striking improvement over conventional designs, the present method and system allow test beds to be manufactured to specification independently. Further, test beds can be made out of glass so that the content can be visually inspected without breaking up the integrity or affecting the chemistry or biology in the test beds. Test beds or microcosms are not from a solid block of material, thereby allowing more flexibility in positioning and assembly. Technology test beds rather than microcosms allow for mimicking of biological, chemical, and physical treatment processes. Biological processes may include the addition of nutrients (i.e., biostimulation) or microorganisms (i.e., bioaugmentation) or a combination of the two. Chemical treatment option may include the injection of chemical oxidation or reduction agents that are incompatible with biological processes, such as injection of potassium permanganate of persulfate. The unit also can be used to evaluate non-sediment media such as iron filing materials, such as, for example, zero valent iron (or even zero valent nanoiron) that can be configured to form a reactive barrier. Reactive barrier technologies are common in remediation and it is desirable to judge their efficacy vis-à-vis bioremediation techniques and other non-barrier approaches. Test beds can be configured to evaluate mutually exclusive remediation approaches and other technologies of interest.

Referring now to FIG. 11 wherein an example of a test bed used in monitored natural attentuation is schematically shown. Following the process from left to right, a test bed is filled with indigenous sediment without adding either nutrients or biomass. Indigenous groundwater containing live bacteria is then pumped through the sediment columns. Naturally occurring bacteria are allowed to settle in the sediment column and grow at the expense of unwanted pollutants.

Referring now to FIG. 12 wherein an example of a test bed used in a bioremediation process is schematically shown. Following the process from left to right, a test bed is filled with indigenous sediment with added nutrients. Indigenous groundwater containing live bacteria is then pumped through the sediment columns containing nutrients. Naturally occurring bacteria are allowed to settle in the sediment column and grow at an enhanced rate while removing unwanted pollutants. A variation of this design employs the addition of additional biomass (native or non-native microorganisms) to accelerate pollutant removal in a process typically referred to as bioaugmentation.

Referring now to FIG. 13 wherein an example of a test bed used in a chemical remediation process is schematically shown. Following the process from left to right, a test bed is filled with indigenous sediment without added nutrients or biomass. Next, indigenous groundwater injected with selected chemicals is pumped through the sediment columns. A resultant chemical reaction occurs in the sediment column detectable immediately by onboard sensors or later during lab analysis of collected effluent and sediment. Instead of indigenous sediment, other chemicals or materials such as iron filings, for example, may be placed in the test beds and the resultant fluid flowing through the test beds may be analyzed for chemical effects.

Referring now to FIG. 14 wherein an example of a test bed used in a physical remediation process is schematically shown. Following the process from left to right, a test bed is filled with indigenous sediment or with groundwater only. Indigenous groundwater is either injected with selected chemicals, biological materials or, used as is, and is pumped through the test bed. The test bed is then exposed to physical treatment such as, for example, a laser beam 400. The physical treatment may include, for example, radiation, light, a laser beam, an electron beam, long wave radiation, short wave radiation, other physical treatments and combinations thereof.

The effect of such treatment can be judged by employing the optional sensing unit to determine the difference caused in chemical composition as a result of the physical treatment. Alternatively, the unit may be retrieved for analysis. In all cases the stored effluent fluid may also be retrieved and analyzed for effects as desired.

Figure 15:
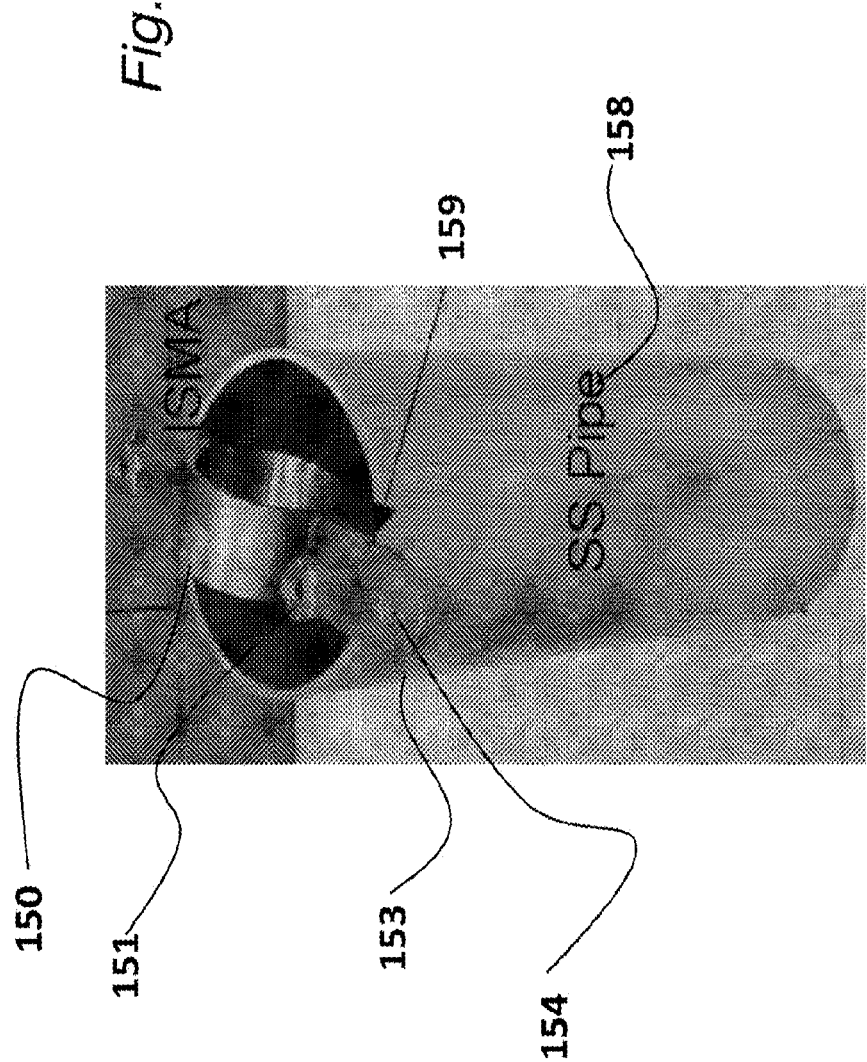
FIG. 15-FIG. 15A schematically show an example of a clamping tool used to position modules into an ISMA assembly on site.
Figure 15A:
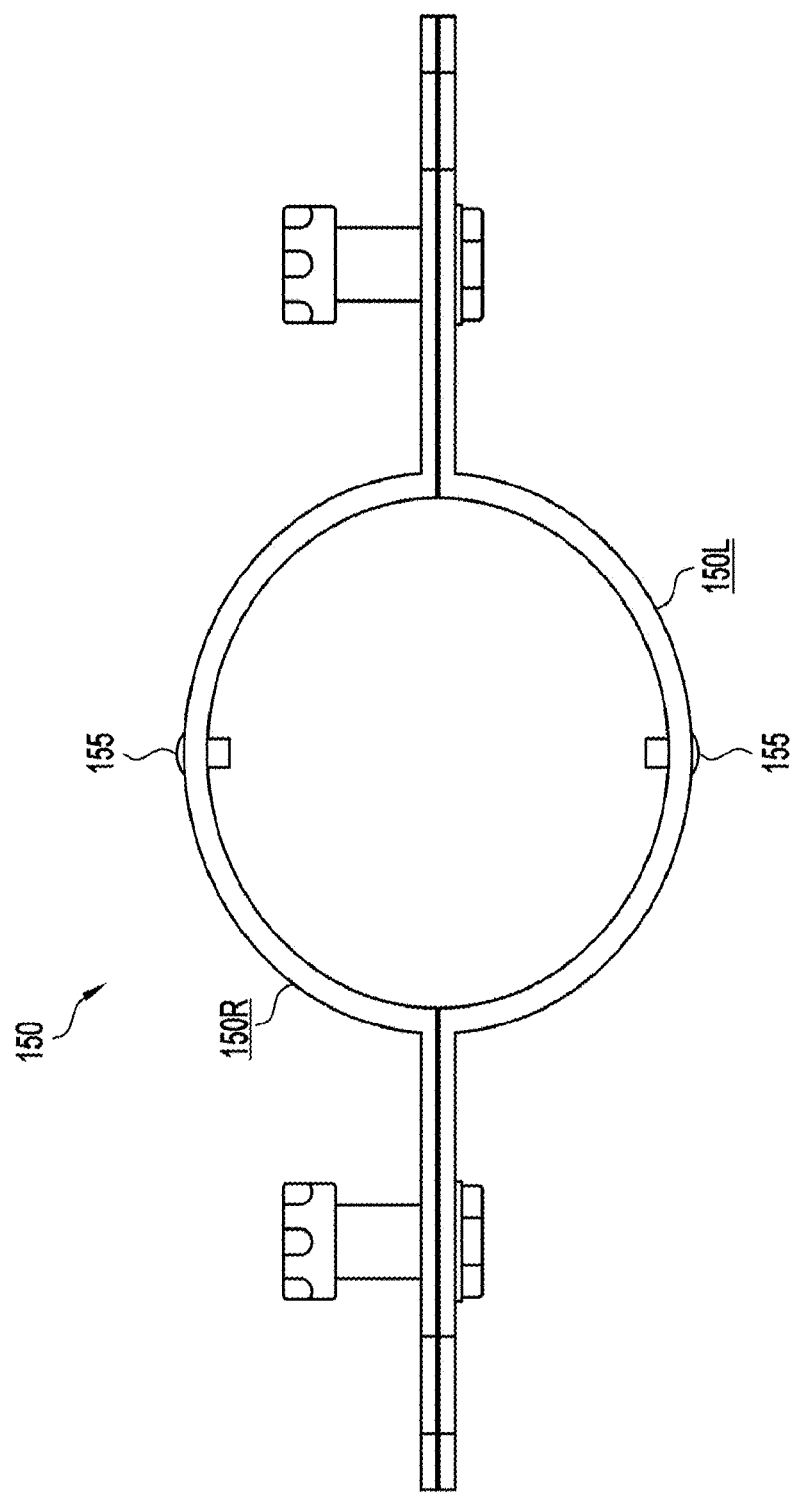

Referring jointly now to FIG. 15 and FIG. 15A wherein an example of a clamping tool used to position modules into an ISMA assembly on site is schematically shown. A clamping tool 150 comprises right and left mating parts 150R and 150L. The mating parts are held together with a set of fasteners 151. A pair of holes 154 are provided for accepting an eye-bolt, for example, for attaching to a cable and external support in order to hold a module in place during module installation on site. A stainless steel pipe 158, or pipe of equivalent material, is sized large enough to allow positioning of an ISMA module over the well. The clamping tool incorporates slots 159 for holding position on the pipe. Inwardly protruding bolts 155, as shown in FIG. 15A, prevent slippage of the module while held in the clamping tool. In an installation operation the clamping tool enables fastening of ISMA modules suspended in the well and transfer of additional ISMA sections from the ground to the borehole. Additional clamping tools may be employed as needed. In one example, the clamping tool is outfitted with two bolts, 2 cables and cable loops to enable suspending ISMA sections from a crane or tripod. An ACME-screw cap with an eye-bolt may also be used for moving additional ISMA modules to the deployment well.

Having described the elements comprising the example embodiment, a description of the operation of the system will now be provided to further explain the invention. It should be evident to those skilled in the art having the benefit of this disclosure that the modular design of the ISMA assembly can be altered to allow for deployment of the device in environments featuring extreme conditions including, but not limited to, extreme pH, temperature, pressure, radiation, gravity conditions different from that of planet Earth, etc. Additionally, many types of microfluidics, filters, sorbent materials, semipermeable membranes and alternative closure mechanisms may be integrated into the sampler to separate in time its inoculation from the incubation period that allows chemical change to take place within the ISMA assembly. Further, the method and system disclosed herein can be used for bioprospecting, risk assessment, and environmental monitoring in any fluid-containing environment including, but not limited to, subsurface environments, surface environments, saturated environments in space, and macroorganisms dead or alive.

One useful method for deploying the unit comprises the following steps:

In the laboratory or in the field, test beds are filled with sediment of choice. Test beds are configured to create an array of test beds each reflecting one treatment technology of interest as well as controls lacking any amendments or changes. A minimum of one test bed is used for each technology tested but the use of replicates is desirable to determine precision and standard deviations ($n=>2$). All connections are made in the unit and the electrical wires and tubing by using quick connects for better service and economy and for minimizing the risk of making a false connection. Configured units are short enough to be handled by one person and can quickly be connected via use of the quick connects. Configured modules may be comprised of one or more of the following and may be shipped to the site by ground or airmail:
   a. Intake module,
   b. Pump module,
   c. Injection module,
   d. Test bed module,
   e. Sensing module, and
   f. Effluent capture module.

When the number of test beds is relatively small, each individual module may contain any combination of the parts taken from the group consisting of a. through f. above.

Modules are assembled in the field by lowering them one by one into the borehole, securing them with the clamp, making the necessary connections using the quick connects for electronics, gas venting and tubing, and lowering the entire device into the borehole using either a tripod and a manual winch, a tripod with a power winch, or a crane or boom in conjunction with a power winch.

The deployed assembly is incubated as long as necessary. Real-time sensors can inform when the experiment is over. Pumps are stopped remotely.

Water samples are retrieved and shipped to analytical laboratories. The modular design allows for continued use with intermittent bag exchanges.

Test bed columns are removed and shipped to analytical laboratories where data are analyzed and reported.

Modules may be returned to the lab for reconfiguration and redeployment. The ISMA assembly is decontaminated to ready the unit for transfer to a new deployment site. All tubing is discarded to prevent cross-contamination from one deployment location to the next. The ISMA assembly is further decontaminated by power washing with a steam washer, which will remove unwanted contaminants from a first site and thus prevent them from migrating from the device into the groundwater of a second deployment site. The process may be repeated at the same or a different site.

The modular design enables deployment of the device in tight spaces with limited overhead room such as in buildings and under bridges substantially according to the following steps:
   1. Measure depth to water in a well.
   2. Pre-load ISMA columns with sediment from the well.
   3. Assemble each of the ISMA device modules separately.
   4. Setup a tripod, crane or boom.

5. Lower the first module into the borehole and secure with clamp.
6. Move the next ISMA module over the well by using the tripod, crane or boom. Make the physical connection between tubing and cables, and join the two modules by the screw or bayonet connector. Repeat extension of the ISMA assembly as often as needed until the whole device is assembled and becomes suspended in the monitoring well.
7. Lower the self-contained device to the bottom of the well.
8. Connect the ISMA assembly to a power source to initiate the pumping of water into the ISMA assembly.
9. Leave the ISMA assembly in place for a sufficient period of time (e.g., 1 hour to 3 months.
10. Check and confirm proper operation if desired.
11. At the end of the incubation period, remove ISMA device using cables and a tripod, boom or crane.
12. Measure depth to water in the well.
13. Disassemble the ISMA assembly. If desired, transfer column effluent water to sample bottles according to standard methods. Ship sediment columns and collected groundwater to a laboratory for analysis.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices, and that various modifications, both as to the equipment details and operating procedures, may be accomplished without departing from the true spirit and scope of the present invention.

What is claimed is:

1. A method for in situ monitoring within a a well comprising:
   locating a housing in the well, wherein a set of pumps and a plurality of test beds are inserted, the set of pumps including more than 1 pump, wherein each of the inserted-set of pumps and test beds comprises a modular design, wherein each pump is dedicated to at least one test bed; and
   controlling each of the set of pumps by signals from the control system to push water from each pump into one of the plurality of separate test beds.

2. The method of claim 1 wherein the set of pumps comprise peristaltic pumps.

3. The method of claim 1 wherein the control system comprises a processor and a communications module.

4. The method of claim 3 further comprising operating one or more sensing units disposed to receive the outflow from the plurality of test beds.

5. The method of claim 4 where the sensing units comprise sensors selected to detect predetermined parameters in the water flowing through the test beds.

6. The method of claim 5 where at least one output signal line from the sensing units is coupled to communicate with a processor.

7. The method of claim 6 wherein the processor communicates received sensor information to a network selected from the group consisting of a private network, WAN, LAN and Internet through communications module, or combinations thereof.

8. The method of claim 1 further comprising operating at least one multichannel valve interposed between the test beds and the sensing units, where the at least one multichannel valve controls fluid flow from the plurality of test beds to the sensing units so as to allow fluid from selected test beds to flow into the sensing units at any point in time.

9. The method of claim 1 further comprising operating at least one injection unit where the at least one injection unit injects test material into at least one of the plurality of separate test beds.

10. The method of claim 9 wherein the injected material is selected from the group consisting of chemical material, biological material, and combinations thereof.

11. The method of claim 1 wherein each of the inserted set of pumps and test beds comprises a modular design allowing for operation of test beds in series to enable turning aerobic groundwater into anaerobic groundwater, which is then fed into a test bed fitted with strict anaerobic bacteria that do not tolerate any oxygen.

12. A method for in situ monitoring within a well comprising:
   locating a housing in the well, wherein a set of pumps and a plurality of test beds are inserted;
   controlling each of the set of pumps by signals from the control system to push water from each pump into one of the plurality of separate test beds where, after flowing through each of the test beds, effluent flows into an effluent storage device; and
   wherein the effluent of one test bed becomes the influent of another test bed.

13. The method of claim 12 further comprising operating switching valves controlled from the ground surface to change the configuration of fluid and/or effluent flow.

14. The method of claim 7 comprising transmitting sensor signals to a receiver station.

15. The method of claim 13 further comprising running multiple test beds in series.

16. The method of claim 1 further comprising powering the system using independent power generated from solar panels, storage batteries and independent power sources, thereby allowing for the unit to operate off the grid with DC current to enable "around-the-clock" operation, day and night.

17. The method of claim 1 further comprising: loading indigenous sediment into one of the test beds; pumping indigenous groundwater containing live bacteria through the sediment test beds; and allowing naturally occurring bacteria to settle and grow in the sediment, and to interact with contaminants.

18. The method of claim 1 further comprising: loading at least one test bed with indigenous sediment with added nutrients; pumping indigenous groundwater containing live bacteria through the sediment containing nutrients; and allowing naturally occurring bacteria to settle in the sediment and grow at an enhanced rate.

19. The method of claim 1 further comprising: loading at least one test bed with a selected material; pumping indigenous groundwater injected with selected chemicals through the sediment columns to promote occurrence of a chemical reaction in the sediment.

20. The method of claim 19 wherein the selected material comprises material selected from the group consisting of indigenous sediment, chemicals, organic material, inorganic material, metals, biological material, iron filings and combinations thereof.

21. The method of claim 1 further comprising: loading a test bed with materials selected from the group consisting of sediment, polymers, catalysts, biological materials, chemicals and groundwater; injecting indigenous groundwater into the test bed and exposing the sediment to physical treatment.

22. The method of claim 21 wherein the physical treatment is selected from the group consisting of radiation, light, a laser beam, an electron beam, long wave radiation, short wave radiation, and combinations thereof.

23. The method of claim 1 further comprising retrieving water samples and shipping the water samples to analytical laboratories.

24. The method of claim 1 further comprising intermittently exchanging an effluent storage bag for continued operation.

25. The method of claim 1 further comprising: deploying multiple ISMA systems in the same area or plume; shutting down individual units in sequence when real-time sensors indicate termination of the experiment is warranted; and retrieving the units in a single field campaign.

26. The method of claim 1 further comprising comparing the efficacy of a resultant remediation achieved after performing the steps of claim 1 against a reactive barrier technology.

* * * * *

UNITED STATES PATENT AND TRADEMARK OFFICE
CERTIFICATE OF CORRECTION

PATENT NO. : 8,691,582 B2  
APPLICATION NO. : 13/681125  
DATED : April 8, 2014  
INVENTOR(S) : Rolf Ulrich Halden Page 1 of 1

It is certified that error appears in the above-identified patent and that said Letters Patent is hereby corrected as shown below:

In the Specification

In Column 1, Line 14:
Delete the following paragraph:
"GOVERNMENT INTEREST STATEMENT
This invention was made with Government support under Contract DoD ESTCP ER-200914 awarded by the United States Department of Defense and Contract NIEHS-R0I 1R01ES015445 awarded by the United States National Insti•tute of Health. The Government has certain rights in the invention."

Insert the following paragraph:
-- GOVERNMENT SUPPORT CLAUSE
This invention was made with government support under RO015445 awarded by the National Institutes of Health. The government has certain rights in the invention. --

Signed and Sealed this
First Day of March, 2022

Drew Hirshfeld
*Performing the Functions and Duties of the
Under Secretary of Commerce for Intellectual Property and
Director of the United States Patent and Trademark Office*